(12) United States Patent
Toriumi et al.

(10) Patent No.: US 9,566,005 B2
(45) Date of Patent: Feb. 14, 2017

(54) MEASURING APPARATUS, MEASURING METHOD, AND PARAMETER SETTING METHOD

(75) Inventors: Yoichi Toriumi, Tokyo (JP); Hideo Kawabe, Saitama (JP); Kenichi Kabasawa, Saitama (JP); Tatsuya Suzuki, Kanagawa (JP); Hirokazu Imai, Chiba (JP); Masatoshi Ueno, Kanagawa (JP)

(73) Assignee: Sony Corporation (JP)

( * ) Notice: Subject to any disclaimer, the term of this patent is extended or adjusted under 35 U.S.C. 154(b) by 470 days.

(21) Appl. No.: 14/356,020

(22) PCT Filed: Sep. 10, 2012

(86) PCT No.: PCT/JP2012/073035
§ 371 (c)(1),
(2), (4) Date: May 2, 2014

(87) PCT Pub. No.: WO2013/069367
PCT Pub. Date: May 16, 2013

(65) Prior Publication Data
US 2014/0303505 A1    Oct. 9, 2014

(30) Foreign Application Priority Data

Nov. 11, 2011  (JP) ................ 2011-247571

(51) Int. Cl.
*G01J 3/00* (2006.01)
*A61B 5/00* (2006.01)
*G01N 21/47* (2006.01)

(52) U.S. Cl.
CPC .......... *A61B 5/0075* (2013.01); *A61B 5/0079* (2013.01); *G01N 21/474* (2013.01); *G01N 2021/4761* (2013.01)

(58) Field of Classification Search
CPC ....... A61B 5/00; A61B 5/0059; A61B 5/0084; A61B 5/0071; A61B 5/0075; G01N 21/31; G01N 21/552; G01N 21/4795; G01J 3/02; G01J 3/42
See application file for complete search history.

(56) References Cited

U.S. PATENT DOCUMENTS 4,880,304 A    11/1989  Jaeb et al.
6,588,118 B2    7/2003  Hellstrom
(Continued)

FOREIGN PATENT DOCUMENTS

JP    63-246138    10/1988
JP    2005-505765 A    2/2005
(Continued)

OTHER PUBLICATIONS

International Search Report mailed Oct. 23, 2012.

*Primary Examiner* — Abdullahi Nur
(74) *Attorney, Agent, or Firm* — Lerner, David, Littenberg, Krumholz & Mentlik, LLP (57) ABSTRACT

There is provided a measuring apparatus, including a light receiving element, provided at a position facing a measurement object region on which is placed a measurement object, which forms an image with light from the measurement object region, light emitting elements, arranged surrounding the light receiving element, which emit light for measuring the measurement object, and reflective optical elements, provided above the light emitting elements, which guide, to the measurement object region, emission light radiated from the light emitting elements. A light receiving surface of the light receiving element and light emission surfaces of the light emitting elements are positioned mutually on a same plane. The emission light radiated from the light emitting elements is reflected by the reflective optical elements, and center lines of the emission light radiated from each of the (Continued)

light emitting elements pass through an approximate center of the measurement object region.

12 Claims, 8 Drawing Sheets

(56) References Cited

U.S. PATENT DOCUMENTS

| | | | |
|---|---|---|---|
| 7,606,608 B2 | 10/2009 | Blank et al. | |
| 2012/0044682 A1* | 2/2012 | Allen | F21V 5/045 362/241 |

FOREIGN PATENT DOCUMENTS

| | | | |
|---|---|---|---|
| JP | 2007-252774 A | 10/2007 | |
| JP | 2007-532183 A | 11/2007 | |
| JP | 2008-086705 A | 4/2008 | |

* cited by examiner

MEASURING APPARATUS, MEASURING METHOD, AND PARAMETER SETTING METHOD

CROSS-REFERENCE TO RELATED APPLICATION

The present application is a national phase entry under 35 U.S.C. §371 of International Application No. PCT/JP2012/073035 filed Sep. 10, 2012, published on May 16, 2013 as WO 2013/069367 A1, which claims priority from Japanese Patent Application No. JP 2011-247571 filed in the Japanese Patent Office on Nov. 11, 2011.

TECHNICAL FIELD

The present disclosure relates to a measuring apparatus, a measuring method and a parameter setting method.

BACKGROUND ART

Spectral measuring methods have been proposed by related art which analyze a measurement object, by irradiating the measurement object with light and measuring reflected light from the measurement object. In such spectral measuring methods, an optical apparatus called an integrating sphere is often used, in order for reflected light from the measurement object to converge without leakage. In spectral measurement methods using such an integrating sphere, a measurement procedure exists which is roughly divided such as into the following two types.

(1) Measuring a spectral reflectance of a measurement object, by multilaterally converging irradiated light from light emitting elements on the measurement object, and guiding the reflected light by collimating in front of a spectral filter.

(2) Measuring a spectral reflectance of a measurement object, by multilaterally converging diffused/reflected light from the measurement object on a spectral filter, and guiding the reflected light by collimating in front of the spectral filter.

Further, a white light source such as a Xenon lamp is used as irradiated light, and spectrally dispersing reflected light from a measurement object into several wavelengths with a spectral filter is generally performed.

Further, for example, spectral measuring apparatuses have also been proposed which measure light from a measurement object, without using an integrating sphere, such as in the following Patent Literature 1.

CITATION LIST

Patent Literature

Patent Literature 1: JP 2007-532183A

SUMMARY OF INVENTION

Technical Problem

However, spectral measuring apparatuses using an integrating sphere such as described above have a problem in that minimization of the apparatus is difficult due to the necessity of using the integrating sphere and optical elements for collimating reflected light. Further, a Xeon light source used as an irradiated light source may be necessary to supply a high power to a light source apparatus in order to obtain emission light, and it will be difficult to save power, and it will be difficult to reduce costs due to including a spectral filter of several wavelengths.

Further, since light from a measurement object is spectrally dispersed by using a diffraction grating in the method of the above described Patent Literature 1, it will be difficult to attain miniaturization as the whole apparatus.

Accordingly, by considering the above described situation, the present disclosure provides a measuring apparatus, measuring method and parameter setting method capable of attaining further miniaturization of the apparatus.

Solution to Problem

According to an embodiment of the present disclosure, there is provided a measuring apparatus, including a light receiving element, provided at a position facing a measurement object region on which is placed a measurement object, which forms an image with light from the measurement object region, a plurality of light emitting elements, arranged surrounding the light receiving element, which emit light for measuring the measurement object, and reflective optical elements, provided above the light emitting elements, which guide, to the measurement object region, emission light radiated from the light emitting elements. A light receiving surface of the light receiving element and light emission surfaces of the plurality of light emitting elements are positioned mutually on a same plane. The emission light radiated from the plurality of light emitting elements is reflected by the reflective optical elements, and center lines of the emission light radiated from each of the light emitting elements pass through an approximate center of the measurement object region.

According to an embodiment of the present disclosure, there is provided a measuring method, including emitting light for measuring a measurement object, from a plurality of light emitting elements which emit light for measuring the measurement object, arranged surrounding a light receiving element provided at a position facing a measurement object region on which is placed the measurement object, the light receiving element forming an image with light from the measurement object region, guiding, to the measurement object region, radiated emission light emitted from each of the plurality of light emitting elements by reflective optical elements provided above the light emitting elements, so that center lines of the radiated emission light pass through an approximate center of the measurement object region, and receiving light reflected from the measurement object region by the light receiving element. A light receiving surface of the light receiving element and light emission surfaces of the plurality of light emitting elements are positioned mutually on a same plane.

According to an embodiment of the present disclosure, there is provided a parameter setting method including setting, in a measuring apparatus, a minimum value of a light amount of light reflected from a measurement object and received by a light receiving element, and determining a size of the light receiving element on the basis of the set minimum value of the light amount of reflected light, the measuring apparatus including the light receiving element provided at a position facing a measurement object region on which is placed the measurement object, the light receiving element forming an image with light from the measurement object region, a plurality of light emitting elements that are arranged surrounding the light receiving element and that emit light for measuring the measurement object, and reflective optical elements that are provided above the light emitting elements and that guide, to the measurement object region, emission light radiated from the light emitting elements, wherein a light receiving surface of the light receiving element and light emission surfaces of the plurality of light emitting elements are positioned mutually on a same plane, and wherein the light radiated from the plurality of light emitting elements is reflected by the reflective optical elements, and center lines of the emission light radiated from each of the light emitting elements pass through an approximate center of the measurement object region, and setting a size of the measurement object region based on a signal-to-noise ratio necessary for the light receiving element and the set minimum value of the light amount of reflected light, and setting a separation distance between the light receiving element and the measurement object based on a light amount incident on the light receiving element and the minimum value of the light amount of reflected light.

According to the preset disclosure, emission light radiated from a plurality of light emitting elements, which are positioned surrounding a light receiving element, is emitted on a same plane as a light receiving surface of the light receiving element, the emitted radiated emission light is irradiated on a measurement object, which is placed in a measurement object region, by reflecting the light with reflective optical elements positioned above the light emitting elements, and diffused/reflected light from the measurement object forms an image on the light receiving element.

Advantageous Effects of Invention

According to the present disclosure such as described above, it is possible to attain further miniaturization of the apparatus.

DESCRIPTION OF EMBODIMENTS

Hereinafter, preferred embodiments of the present invention will be described in detail with reference to the appended drawings. Note that, in this specification and the drawings, elements that have substantially the same function and structure are denoted with the same reference signs, and repeated explanation is omitted.

The description will be given in the following order.
(1) The first embodiment
 (1-1) Regarding the overall configuration of the measuring apparatus
 (1-2) Regarding the configuration of the optical system
 (1-3) Regarding the parameter setting method
(2) Application example of the measuring apparatus The First Embodiment <Regarding the Overall Configuration of the Measuring Apparatus>

Figure 1A:
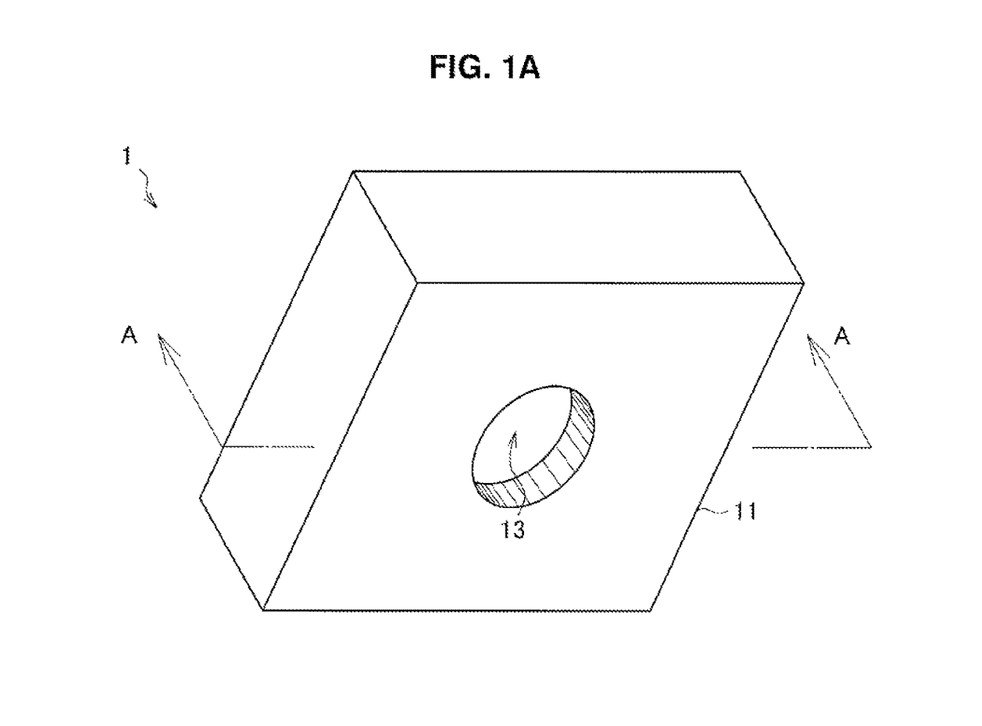
FIG. 1A is an explanatory diagram which schematically shows an overall configuration of a measuring apparatus according to a first embodiment of the present disclosure.
Figure 1B:
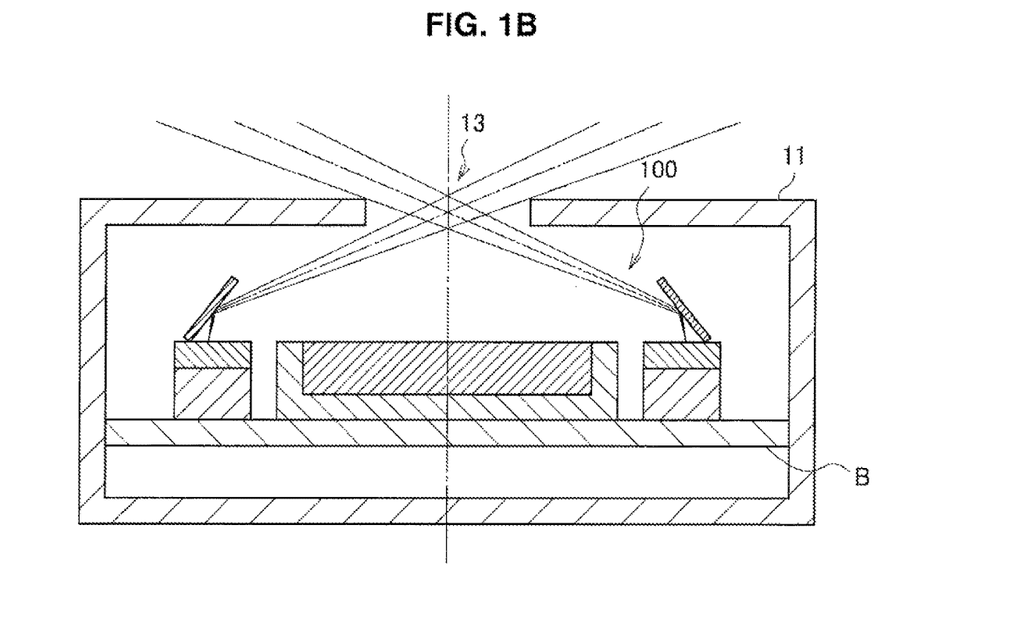
FIG. 1B is an explanatory diagram which schematically shows an overall configuration of the measuring apparatus according to the same embodiment.

First, an overall configuration of a measuring apparatus according to a first embodiment of the present disclosure will be simply described with reference to FIG. 1A and FIG. 1B. FIG. 1A and FIG. 1B are explanatory diagrams which schematically show an overall configuration of a measuring apparatus according to the present embodiment.

As shown in FIG. 1A, a measuring apparatus 1 according to the present embodiment has a housing 11 constituted from an arbitrary material, and includes an opening section 13 in one part of the housing 11. While the shape of the opening section 13 is circular in FIG. 1A, the shape of the opening section 13 is not limited to a circular shape, and may be a polygonal shape or may be an oval shape. A measurement object is placed in the portion of this opening section 13, and the measuring apparatus 1 according to the present embodiment performs measurements for the placed measurement object.

Here, the measurement object placed in the opening section 13 is preferably organic matter, in which light reflected from the measurement object is extremely easily to be diffused or scattered by a Mie scattering effect or the like. For example, an object which contains organic matter such as an organic light emitting layer in an organic EL display, the skin surface of a human body, or various types of cells, can be included as such organic matter.

FIG. 1B is a cross-sectional view which shows a cross-section cut through FIG. 1A by an A-A cross-section line.

As shown in FIG. 1B, the interior of the housing 11 is a hollow space, and an optical system 100 of the measuring apparatus 1 according to the present embodiment is mounted in the interior of the housing 11. Further, in order to suppress reflections of light leaking from the optical system 100, it is preferable for the inner wall of the housing 11 to be black or a dark color tone equivalent to black.

Here, a detailed description will again be made hereinafter for the optical system 100 mounted in the interior of the housing 11. Further, while FIG. 1B is illustrated so that only the optical system 100 is present in the interior of the housing 11, arbitrary units other than the optical system 100 may be mounted in the interior of the housing 11, in a range which does not influence the measurement process by the optical system 100.

<Regarding the Configuration of the Optical System>

To continue, an optical system included in the measuring apparatus 1 according to the present embodiment will be described in detail with reference to FIG. 2A to FIG. 2C.

Figure 2A:
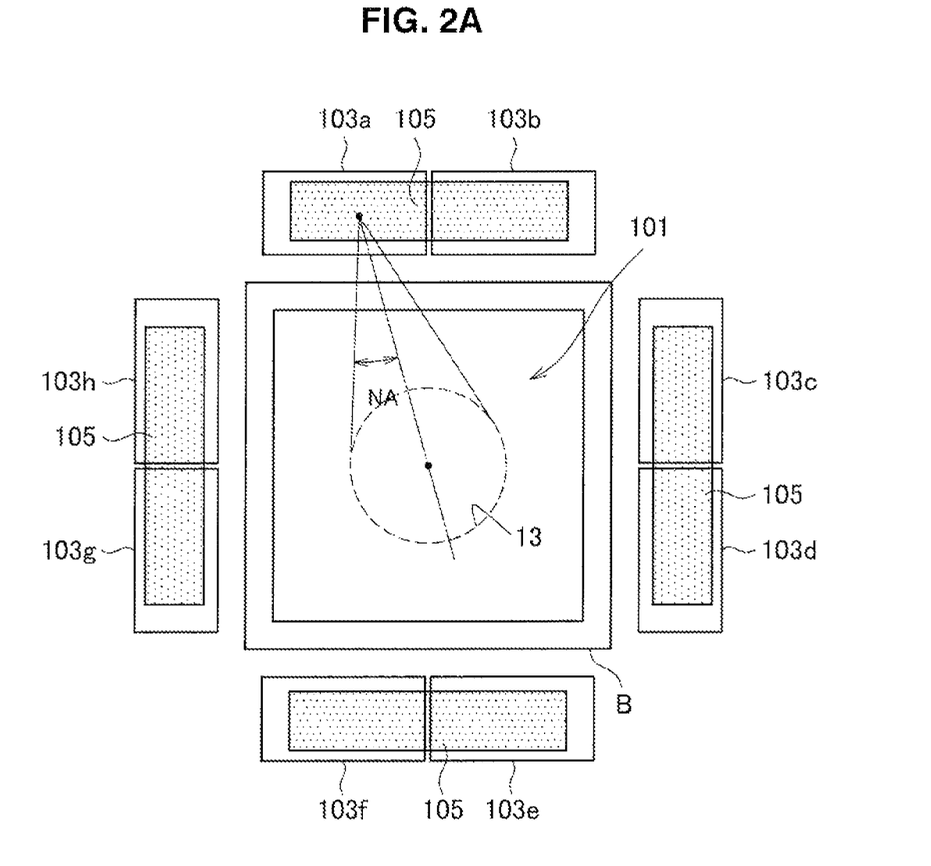
FIG. 2A is an explanatory diagram which shows an example of an optical system included in the measuring apparatus according to the same embodiment.
Figure 2B:
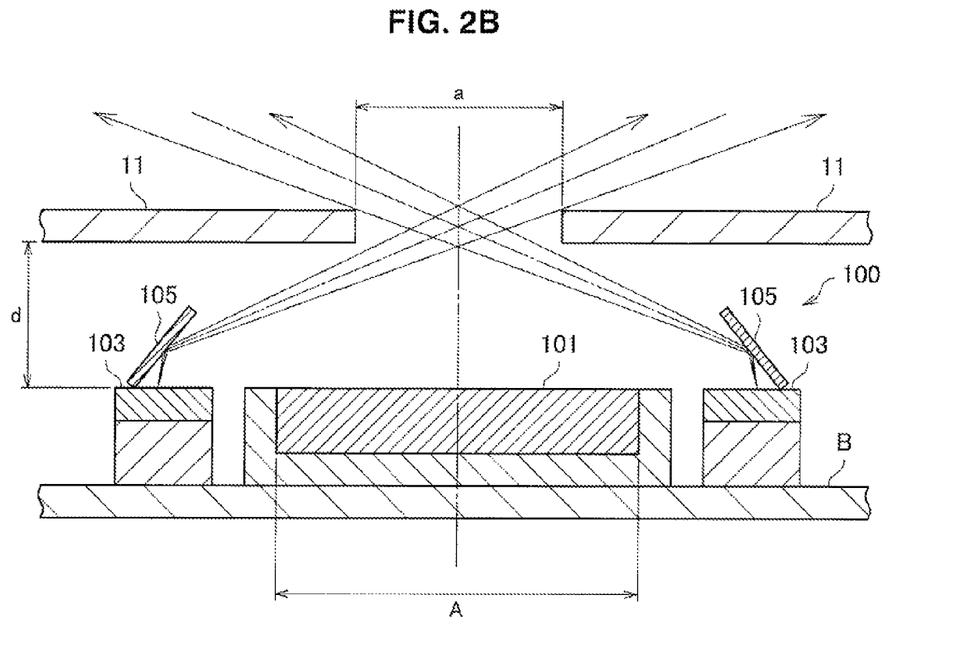
FIG. 2B is an explanatory diagram which shows an example of the optical system included in the measuring apparatus according to the same embodiment.

FIG. 2A is a plan view in the case of viewing the optical system 100 according to the present embodiment from the side of the opening section 13, and FIG. 2B is a cross-sectional view in the case of cutting the optical system 100 according to the present embodiment by the center line of FIG. 2A. Further, FIG. 2C is an explanatory diagram which shows an enlargement near a light emitting element 103 of the optical system 100 according to the present embodiment. Note that, hereinafter, a description will be made in the case where the skin surface of a human body is placed in the opening section 13, and the skin surface placed in the opening section 13 becomes a measurement object region.

As shown in FIGS. 2A and 2B, the optical system 100 according to the present embodiment has a light receiving element 101 arranged on a housing unit B having an arbitrary shape such as a substrate, and a plurality of light emitting elements 103 arranged on the housing unit B having an arbitrary shape such as a substrate, and reflective optical elements 105 such as mirrors.

Light scattered and reflected from the measurement object region on which is placed the measurement object forms an image on the light receiving element 101. The light receiving element 101 generates data or the like which represents a light amount of the light forming an image, in accordance with a light amount of light forming an image on a light receiving surface. For example, while a photodiode can be included as such a light receiving element 101, the light receiving element 101 according to the present embodiment is not limited to that described above, and it is possible to use other optical sensors.

As shown in FIG. 2A and FIG. 2B, this light receiving element 101 is arranged so as to face the opening section 13 included in the housing 11 of the measuring apparatus 1, and a center of the opening section 13 faces a center of the light receiving element 101.

Further, in the measuring apparatus 1 according to the present embodiment, in order to receive light reflected from the measurement object (for example, the skin surface of a human body) without leakage as much as possible, the light receiving element 101 has a light receiving area sufficiently larger than the area of the opening section 13, such as shown in FIG. 2A. In addition, in the measuring apparatus 1 according to the present embodiment, in order to receive light reflected from the measurement object without leakage as much as possible, a separation distance d between the light receiving element 101 and the opening section 13 is made sufficiently small. In this way, in the measuring apparatus 1 according to the present embodiment, the thickness of the measuring apparatus 1 can be reduced, and it becomes possible to attain miniaturization of the measuring apparatus.

Here, while the light receiving element 101 may be arbitrarily set in accordance with an accuracy or the like to be obtained for the measuring apparatus 1, with regards to how much of the light reflected from the measurement object is received, it is preferable to be set to 95% or more, for example, on the basis of a light amount of the light reflected from a white calibration plate (white light diffusion/reflection plate) such as a Gauss calibration plate.

Note that, while it is preferable for the light amount reflected from the measurement object and received by the light receiving element 101 to be large, it may be necessary to use an integrating sphere, in order to receive 100% of the light reflected from the measurement object, and there is the possibility that the set dimensions of the optical system, and consequently the size of the measuring apparatus, will become larger. However, in the measuring apparatus 1 according to the present embodiment, as will be described in detail hereinafter, the three parameters of the size of the light receiving element, the size of the opening section, and the separation distance between the light receiving element and the opening section, are set in a range in which a trade-off relation is established between the light amount of reflected light to be received in the light receiving element 101, and the light amount incident on the light receiving element to be obtained for ensuring a signal-to-noise ratio (SNR) in the light receiving element, and miniaturization of the measuring apparatus is attempted.

Further, as shown in FIGS. 2A and 2B, a plurality of light emitting elements 103a to 103h (hereinafter, collectively called light emitting elements 103) are arranged along the 4 sides of the light receiving element 101, surrounding the light receiving element 101. As shown in FIG. 2B, the light emission surfaces of these light emitting elements 101 are present on a same plane as the light receiving surface of the light receiving element 101. Here, the light emission surfaces of the plurality of light emitting elements 103 and the light receiving surface of the light receiving element 101 may be mutually present on a same plane, and the light receiving element 101 and the plurality of light emitting elements 103 may be arranged on the same substrate, or may be arranged on different substrates.

For example, it is possible to use light emitting diodes (LEDs) as such light emitting elements 103. Further, light emitting elements which emit radiated light of prescribed wavelengths may be used as the light emitting elements 103 according to the present embodiment, or light emitting elements which radiate white light, and a filter for obtaining light of desired wavelengths, may be used in combination.

In the measuring apparatus 1 according to the present embodiment, N (8 in FIG. 2A) light emitting elements 103 such as described above are arranged surrounding the light receiving element 101, and emit light of M (M≤N) types of wavelengths. Further, wavelengths of radiated light emitted from the light emitting elements 101 may be arbitrarily selected in accordance with a classification of the measurement object, the substance set as the measurement object, or the like.

Here, in the case where (the wavelength number M<the number N of light emitting elements), it becomes possible to have a plurality of arrangements for light which emits light of some wavelengths. In this case, in the measuring apparatus 1 according to the present embodiment, it is preferable to arrange the plurality of light emitting elements 103, by prioritizing from the narrowest allowable wavelength width, or from the smallest light amount from the light emitting elements themselves or via a filter.

Hereinafter, a specific description will be made, with the skin surface of a human body as an example, related to a selection method of wavelengths in the case where M<N.

Figure 3:
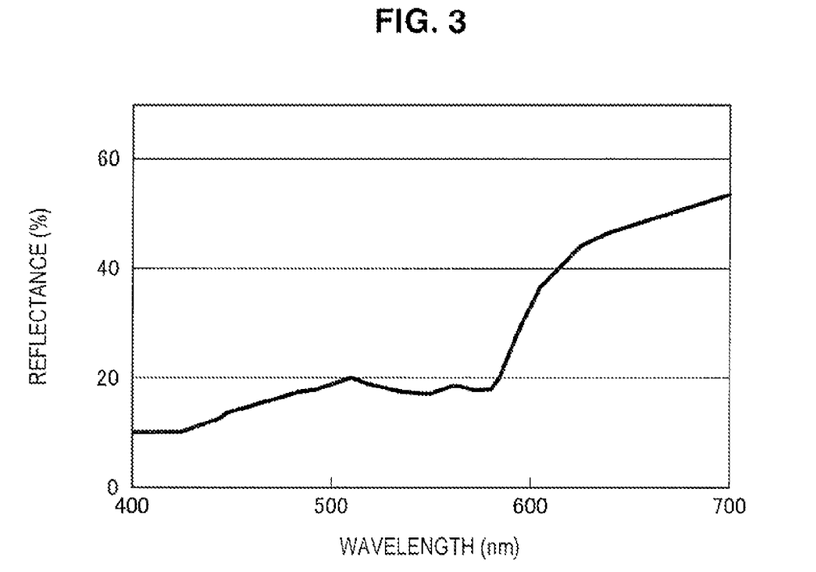
FIG. 3 is a graph figure which shows wavelength characteristics of the reflectance of skin.

FIG. 3 is a measurement result in which the reflectance of human skin has been measured in a visible light wavelength region (400 nm to 700 nm). As is evident from FIG. 3, human skin has a reflectance which gradually increases from 400 nm up to the region in the vicinity of 500 nm, a reflectance which slightly decreases after this up to the region in the vicinity of 600 nm, and a reflectance which suddenly increases from the vicinity of 600 nm up to the vicinity of 650 nm.

Here, in the case where human skin is set as a measurement object, by focusing on the entire visible light wavelength region such as shown in FIG. 3, a light source capable of emitting light of the entire visible light wavelength region may be necessary, and a dispersion element such as a diffraction grating may be necessary in order to specify a light amount for each wavelength. As a result of this, it is expected that it will be difficult to attain miniaturization of the measuring apparatus.

Accordingly, in the measuring apparatus 1 according to the present embodiment, by selecting M types of characteristic wavelengths for a phenomenon or substance set as a measurement object, more efficient measurement of the phenomenon or substance set as the measurement object will be implemented, without using a special light source or dispersion element. For example, in the case of human skin shown in FIG. 3, the characteristic wavelength positions in the spectrum are the 5 points shown in FIG. 4. Accordingly, in the measuring apparatus 1 according to the present embodiment, by focusing on the 5 types of wavelengths shown in FIG. 4, human skin will be measured more efficiently. Note that, 5 such types of wavelengths are useful wavelengths in the case where various types of hemoglobin, such as oxyhemoglobin, glycohemoglobin and deoxyhemoglobin present within human blood, are set as a measurement object.

Further, when focusing on the shape of the spectrum shown in FIG. 3, since the reflectance suddenly rises in the vicinity of a wavelength of 580 nm, it can be understood that the allowable wavelength width for light of this wavelength is narrow, in the case of focusing on light of a wavelength of 580 nm. Conversely, since the reflectance gradually changes in the vicinity of a wavelength of 540 nm, it can be understood that the allowable wavelength width for light of this wavelength is set to be relatively large, in the case of focusing on light of a wavelength of 540 nm. From such a viewpoint, when considering the wavelength widths of the 5 wavelengths shown in FIG. 4, the following can be set, for example.

Figure 4:
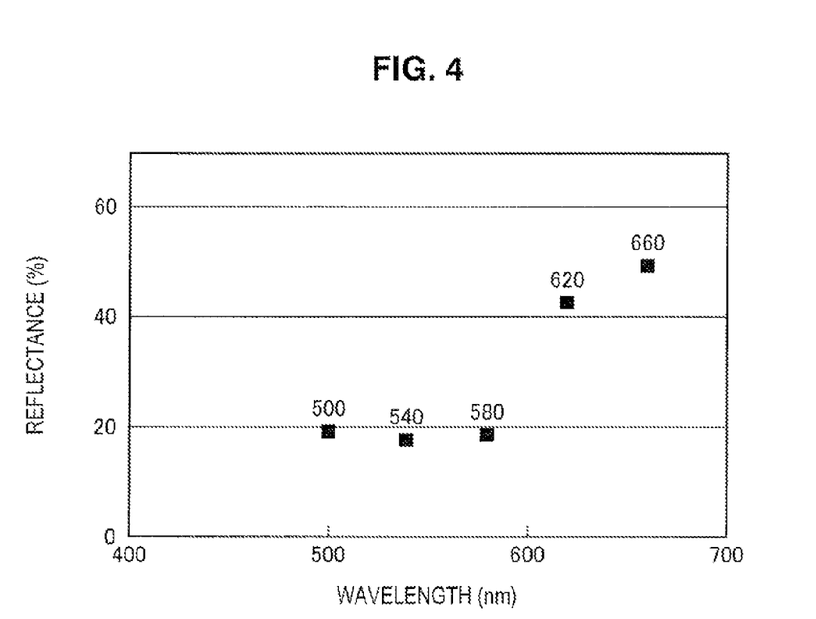
FIG. 4 is a graph figure which shows wavelength characteristics of the reflectance of skin.

$\lambda_1$(blue): 500±25 nm
$\lambda_2$(green): 540±15 nm
$\lambda_3$(yellow): 580±5 nm
$\lambda_4$(red): 620±15 nm
$\lambda_5$(red): 660±15 nm Here, in the case where the light emitting elements 103 are mounted which emit the above described 5 types of wavelengths, in the optical system 100 shown in FIG. 2A, for example, one of each of the light emitting elements capable of emitting light of the wavelengths of $\lambda_1$ and $\lambda_2$, and two of each of the light emitting elements capable of emitting light of the wavelengths of $\lambda_3$, $\lambda_4$ and $\lambda_5$, can be arranged in accordance with the light amount and allowable wavelength widths of wavelengths to be focused on. Here, in the case where a plurality of light emitting elements 103 are mounted capable of emitting light of the same wavelength, it is preferable that the light emitting elements capable of emitting light of the same wavelength are arranged so as to be positioned symmetrically on the basis of the center of the light receiving element 101.

The radiated light emitted from each of the light emitting elements 103 is set as light of a prescribed numerical aperture NA by an aperture or light converging element such as a lens (not shown in the figures) included on the light emitting elements 103, and proceeds to the reflective optical elements 105 such as mirrors. Here, it is preferable that the value of the above described numerical aperture NA is set as 0.2. Since the ratio of radiated light not irradiated on the measurement object region will increase, when the numerical aperture NA becomes larger than 0.2, it is not preferable.

Figure 2C:
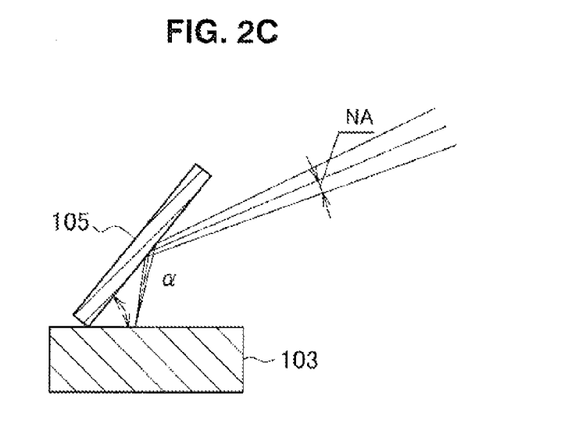
FIG. 2C is an explanatory diagram which shows an example of the optical system included in the measuring apparatus according to the same embodiment.

As shown in FIG. 2A to FIG. 2C, the reflective optical elements 105 such as mirrors are included above the light emitting elements 103, and radiated emission light emitted from the light emitting elements 103 is guided, to the measurement object region, so that the center line of this radiated emission light passes through an approximate center of the measurement object region. These reflective optical elements 105 may be individually included directly above each of the light emitting elements 103, or a common reflective optical element 105 may be included for a plurality of the light emitting elements 103, such as shown in FIG. 2A, for example.

Further, the size of an angle (angle α in FIG. 2C) formed by the light emission surfaces of the light emitting elements 103 and the reflection surfaces of the reflective optical elements 105 is set in accordance with a separation distance d between the light receiving element 101 and the opening section 13, or in accordance with a numerical aperture NA or the like of the radiated emission light.

In the measuring apparatus 1 according to the present embodiment, by including the reflective optical elements 105 above the light emitting elements 103, it becomes possible to irradiate emission light radiated from the light emitting elements 103 to an approximate center of the measurement object region (in other words, the opening section 13), even in the case where the separation distance d shown in FIG. 2B is small, and can contribute to miniaturization (thinning) of the measuring apparatus 1.

Heretofore, an overall configuration of the measuring apparatus 1 according to the present embodiment has been described in detail with reference to FIG. 1A to FIG. 4.

In the measuring apparatus 1 according to the present embodiment, by having a configuration such as described above, radiated emission light for measuring a measurement object is emitted, to the measurement object region on which is placed a measurement object, from the plurality of light emitting elements 103 included surrounding the light receiving element 101, the radiated emission light is guided, to the measurement object region, by the reflective optical elements 105 included above the light emitting elements, so that the center line of the radiated emission light passes pass through an approximate center of the measurement object region, and reflected light scattered/diffused by a Mie scattering effect or the like of the measurement object forms an image on the light receiving element 101.

<Regarding the Parameter Setting Method>

Figure 5:
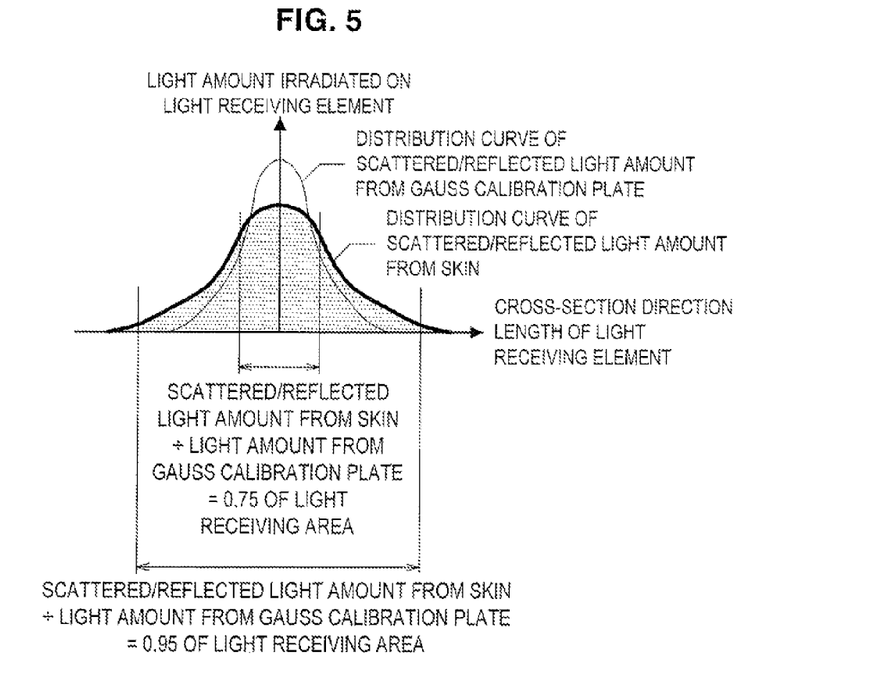
FIG. 5 is a graph figure which schematically shows a distribution of a light amount reflected from a measurement object region incident on a light receiving element.
Figure 6:
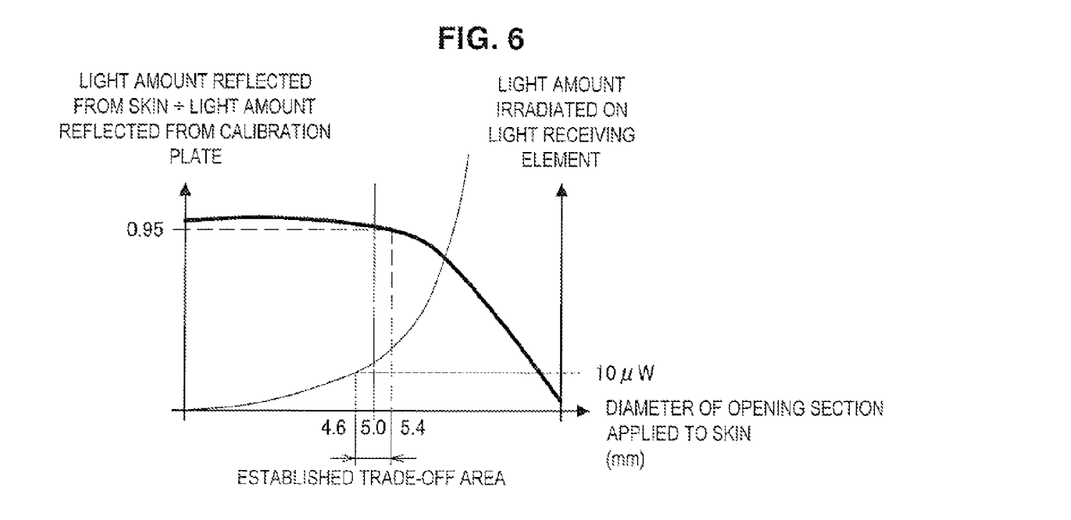
FIG. 6 is a graph figure which schematically shows a relation between the light amount reflected from the measurement object region and a signal-to-noise ratio of the light receiving element.
Figure 7:
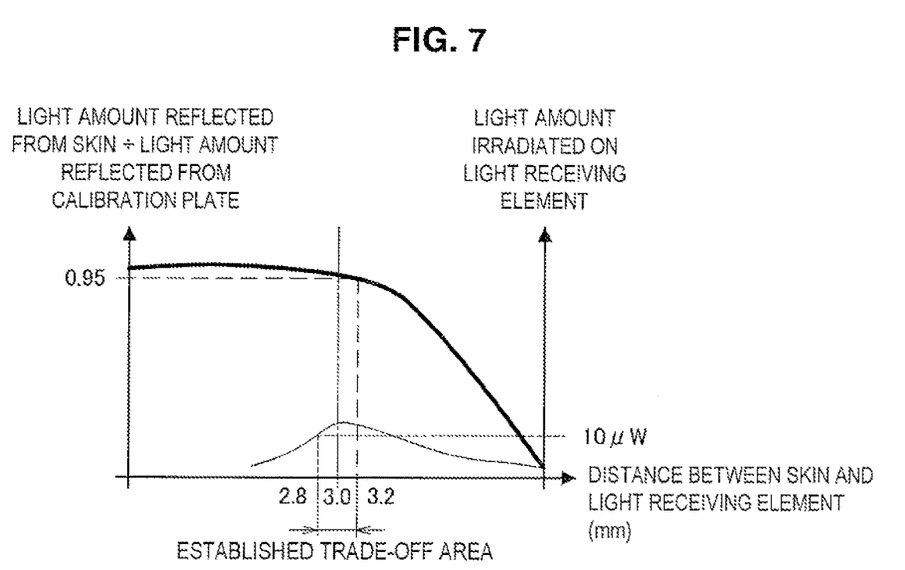
FIG. 7 is a graph figure which schematically shows a relation between the light amount reflected from the measurement object region and the light amount incident on the light receiving element.

Hereinafter, a setting method of design parameters in the measuring apparatus 1 according to the present embodiment will be described in detail, and a setting example of each parameter will be specifically described, with reference to FIG. 5 to FIG. 7. FIG. 5 is a graph figure which schematically shows a distribution of a light amount reflected from the measurement object region incident on the light receiving element. FIG. 6 is a graph figure which schematically shows a relation between the light amount reflected from the measurement object region and a signal-to-noise ratio of the light receiving element. FIG. 7 is a graph figure which schematically shows a relation between the light amount reflected from the measurement object region and the light amount incident on the light receiving element.

For example, the size of the light receiving element 101, the size of the opening section and the separation distance between the light receiving element 101 and the opening section 13 can be included as the main parameters when designing the measuring apparatus 1 according to the present embodiment. How these design parameters are set will be important, in order to attain miniaturization of the measuring apparatus 1 while achieving a desired measurement accuracy.

Since the measuring apparatus 1 according to the present embodiment performs measurements of a desired substance, based on light reflected from a measurement object, how much of the reflected light is capable of being received will become an important factor. Accordingly, in a parameter setting method in the measuring apparatus 1 according to the present embodiment, first a setting is performed for a light amount of reflected light capable of being received by the light receiving element 101 (in other words, a minimum value of a light amount of reflected light capable of being received by the light receiving element 101).

Afterwards, in the parameter setting method according to the present embodiment, the size of the light receiving element 101, the size of the measurement object region (opening section 13), and the separation distance between the light receiving element 101 and the opening section 13, are each set independent of each other, based on the set light amount of reflected light.

[Setting Method of the Size of the Light Receiving Element]

First, a setting method of the size of the light receiving element will be described with reference to FIG. 5.

FIG. 5 is a graph figure which shows a light amount distribution of light reflected from the measurement object incident on the light receiving element. The horizontal axis of the graph figure represents the length of a cross-section direction of the light receiving element (for example, the length A in FIG. 2B), and the vertical axis of the graph figure represents the light amount of reflected light incident on the light receiving element.

A distribution of a diffused/reflected light amount from a Gauss calibration plate, which is an example of a white calibration plate, is described in the graph figure shown in FIG. 5. As shown in FIG. 5, the distribution of a diffused/reflected light amount from the Gauss calibration plate is an approximate Gaussian distribution. Further, a distribution of scattered/reflected light from skin is also described in combination in the graph figure shown in FIG. 5. As is evident from FIG. 5, since there is Mie scattering or the like it can be understood that the distribution of scattered/reflected light from skin is wider than the distribution of scattered/reflected light from the Gauss calibration plate. Therefore, in the case where the size (the cross-section direction length) of the light receiving element is small, the light receiving element 101 is not able to receive scattered/reflected light of a sufficient light amount, and the measurement accuracy will be reduced.

In the parameter setting method according to the present embodiment, a minimum value of the light amount of reflected light capable of being received by the light receiving element 101 is represented by a ratio on the basis of the diffused/reflected light amount from the Gauss calibration plate. The diffused/reflected light amount from the Gauss calibration plate is represented as an area of the region surrounded by the distribution curve of the diffused/reflected light amount from the Gauss calibration plate shown in FIG. 5, and the horizontal axis of the graph. Therefore, when a setting value of the light amount of reflected light capable of being received by the light receiving element 101 is set, the width of the range of the distribution curve for implementing the setting value of the light amount can be determined, by focusing on the area of the distribution curve of the diffused/reflected light amount from skin.

For example, in the case where 95% of the diffused/reflected light amount from the Gauss calibration plate is to be received by the light receiving element 101, an area is provided which becomes 95% of the diffused/reflected light amount from the Gauss calibration plate centered on the origin point, and a range of the distribution curve of the scattered/reflected light amount of skin is determined. The size of a range such as this provided can be set as the size of the light receiving element 101 (cross-section direction length). By such a method, the cross-section direction length of the light receiving element 101, which is capable of implementing a light receiving amount of 95%, can be set as 10 mm. Therefore, in the measuring apparatus 1 according to the present embodiment, it becomes clear that it is possible to use a light receiving element of 10 mm×10 mm as the light receiving element 101.

[Setting Method of the Size of the Opening Section]

To continue, a setting method of the size of the opening section will be described with reference to FIG. 6.

FIG. 6 is a graph figure which shows a state of a change of the light amount reflected from skin in the case where the size of the opening section (specifically, a diameter a of the circular opening section shown in FIG. 2B) is allowed to change, and a state of a change of the light amount incident on the light receiving element 101. The horizontal axis of the graph figure represents the diameter of the opening section 13, and the vertical axis of the graph figure represents the ratio of the light amount reflected from skin, and the light amount ($\mu$W) which may be incident on the light receiving element 101.

The graph figure shown by the narrow line in FIG. 6 shows a change of the light amount of light reflected from skin which may be incident on the light receiving element 101. Since the area of the skin placed on the opening section 13 increases as the size of the opening section 13 increases, the light amount of reflected light to be scattered from the skin towards the light receiving element 101 will increase, and the light amount which may be incident on the light receiving element 101 will increase, such as shown in FIG. 6.

The graph figure shown by the thick line in FIG. 6 shows a change of the ratio of the light amount reflected from the skin to be received by a light receiving element having some fixed size (in FIG. 6, a light receiving element of 10 mm×10 mm). While the size of the light amount reflected from the skin increases as the size of the opening section 13 increases, since reflected light which is not able to be received will increase, in the case where the size of the light receiving element 101 is fixed when the size of the opening section 13 exceeds some threshold, the ratio of the light amount reflected from the skin to be received by the light receiving element 101 will suddenly decrease.

In this way, it can be understood that there is a relation of a mutual trade-off between the reflected light amount received by the light receiving element 101 having some fixed size, and the reflected light amount which may be incident on the light receiving element.

In order to maintain a signal-to-noise ratio (SNR) of the signals detected by the light receiving element 101, a certain degree of the light amount incident on the light receiving element 101 is necessary. In the case where a threshold of an incident light amount for maintaining a prescribed signal-to-noise ratio is 10 $\mu$W, it is preferable that the size of the opening section 13 is set to 4.6 mm or more, such as shown in FIG. 6. Conversely, in order for the light receiving element 101 to receive a reflected light amount of 95% or more, it is preferable that the size of the opening section 13 is set to 5.4 mm or less, such as shown in FIG. 6. Therefore, by setting the size of the opening section 13 from 4.6 mm to 5.4 mm (5.0 mm±0.4 mm), it becomes possible to detect 95% or more of the light amount reflected from skin, while maintaining a signal-to-noise ratio of the detected signals.

[Setting Method of the Separation Distance Between the Light Receiving Element and the Opening Section]

To continue, a setting method of the separation distance between the light receiving element 101 and the opening section 13 will be described with reference to FIG. 7.

FIG. 7 is a graph figure which considers an opening section having some fixed size and a light receiving element having some fixed size, focuses on the case where a separation distance (distance d in FIG. 2B) between the opening section (in other words, skin which is the measurement object) and the light receiving element is allowed to change, and shows a state of a change of the light amount reflected from the skin, and a state of a change of the light amount incident on the light receiving element 101. The horizontal axis of the graph figure represents the separation distance between the light receiving element and the opening section, and the vertical axis of the graph figure represents the ratio of a light amount reflected from the skin, and the light amount (μW) which may be incident on the light receiving element 101.

The graph figure shown by the narrow line in FIG. 7 shows a change of the light amount of light reflected from the skin which may be incident on the light receiving element 101. While the light amount received by the light receiving element 101 increases as the separation distance d increases, when the separation distance d exceeds some threshold, the reflected light from the gap between the opening section 13 and the light receiving element 101 will not be incident on the light receiving element 101, and the incident light amount will decrease.

The graph figure shown by the thick line in FIG. 7 shows a change of the ratio of the light amount reflected from the skin to be received by a light receiving element having some fixed size (in FIG. 7, a light receiving element of 10 mm×10 mm). In the case where the size of the light receiving element 101 is fixed when the separation distance d exceeds some threshold, the reflected light which is not able to be received will increase. Therefore, as shown in FIG. 7, the ratio of the light amount reflected from the skin to be received by the light receiving element 101 will suddenly decrease.

In this way, it can be understood that there is a relation of a mutual trade-off between the reflected light amount received by the light receiving element 101 having some fixed size, and the reflected light amount which may be incident on the light receiving element.

In order to maintain a signal-to-noise ratio (SNR) of signals detected by the light receiving element 101, a certain degree of the light amount incident on the light receiving element 101 is necessary. In the case where a threshold of an incident light amount for maintaining a prescribed signal-to-noise ratio is 10 μW, it is preferable that the size of the separation distance d is set to 2.8 mm or more, such as shown in FIG. 7. Conversely, in order for the light receiving element 101 to receive a reflected light amount of 95% or more, it is preferable that the size of the opening section 13 is set to 3.2 mm or less, such as shown in FIG. 7. Therefore, by setting the size of the separation distance d from 2.8 mm to 3.2 mm (3.0 mm±0.2 mm), it becomes possible to detect 95% or more of the light amount reflected from the skin, while maintaining a signal-to-noise ratio of the detected signals.

When the values of each of the set parameters are collected, based on a design criteria such as described above, they will be as follows.

In the case where the minimum value of a light amount reflected from the skin is set to 95%

Size of the light receiving element 101: 10 mm×10 mm

Size (diameter) of the opening section 13: 5 mm±0.4 mmØ

Separation distance between the light receiving element 101 and the opening section 13: 3 mm±0.2 mm Further, in order for radiated light of a numerical aperture NA=0.2 to be guided to the opening section 13 in the measuring apparatus 1 having parameters such as described above, it is evident that a setting angle α of the reflective optical elements 105 in FIG. 2C may be set to 51°.

By setting parameters based on such a design criteria, in the measuring apparatus 1 according to the present embodiment, it becomes possible to detect reflected light by the light receiving element more accurately, even though the radiated emission light from the light emitting elements is irradiated on the measurement object at an acute angle from the small gap between the light receiving element and the opening section.

Heretofore, a setting method of design parameters in the measuring apparatus 1 according to the present embodiment has been described in detail, and a setting example of each parameter has been specifically described, with reference to FIG. 5 to FIG. 7.

<Application Example of the Measuring Apparatus>

Figure 8:
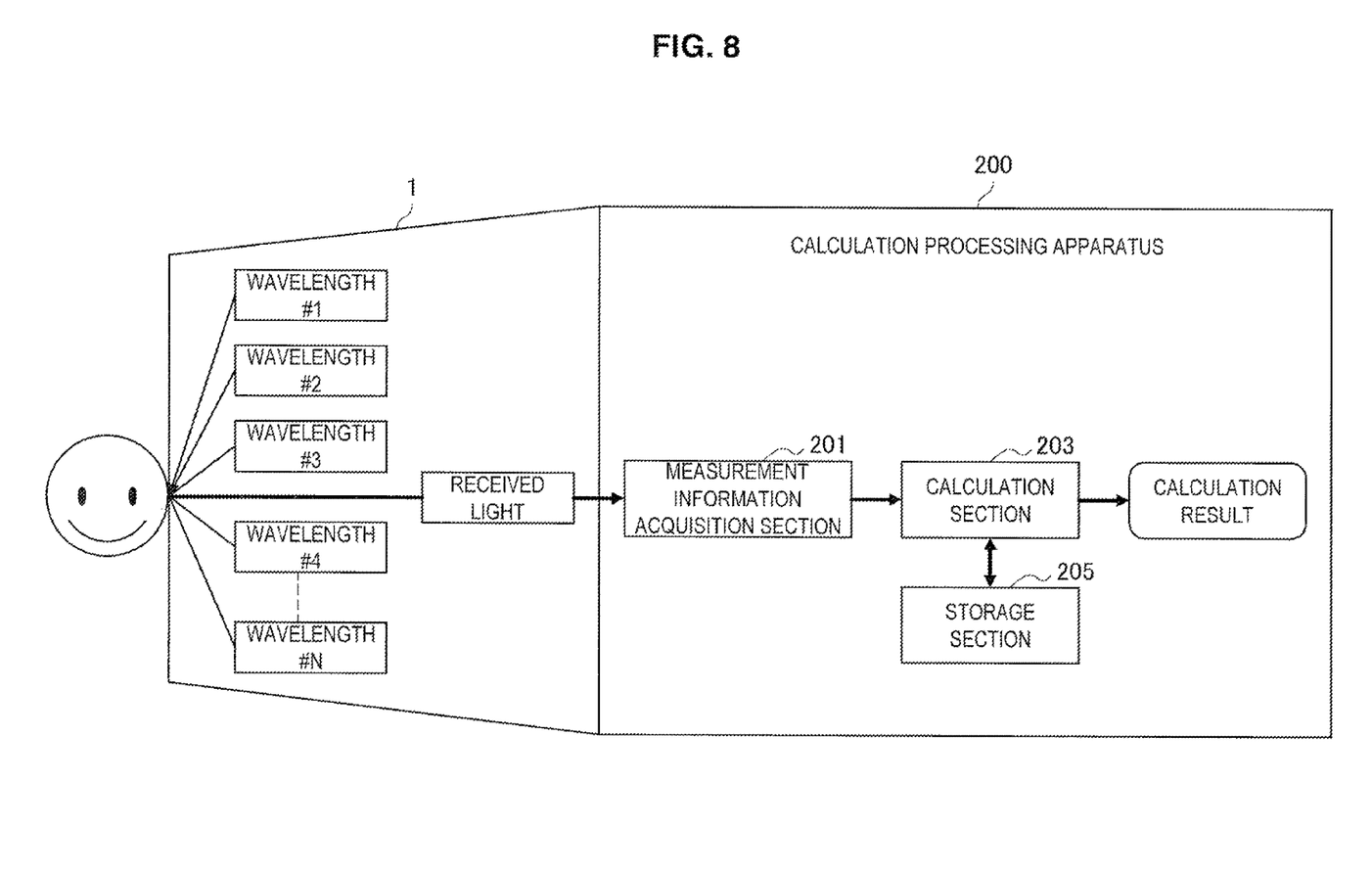
FIG. 8 is an explanatory diagram for describing an application example of the measuring apparatus according to an embodiment of the present disclosure.
Figure 9:
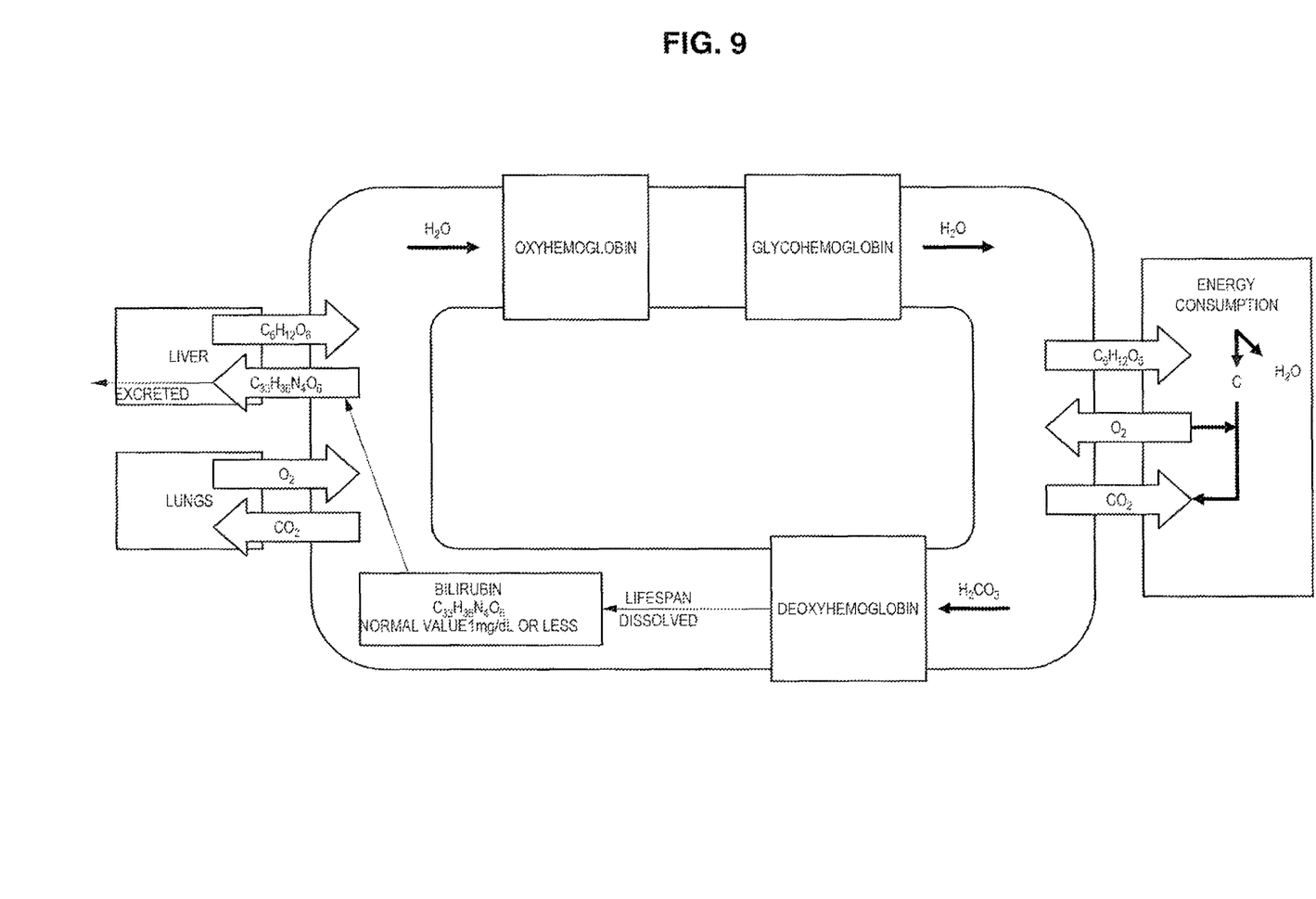
FIG. 9 is an explanatory diagram for describing an application example of the measuring apparatus according to an embodiment of the present disclosure.

To continue, an application example of the measuring apparatus according to the present embodiment will be simply described with reference to FIG. 8 and FIG. 9. FIG. 8 and FIG. 9 are explanatory diagrams for describing an application example of the measuring apparatus according to an embodiment of the present disclosure.

For example, as shown in FIG. 8, by applying the measuring apparatus 1 according to an embodiment of the present disclosure in combination with a calculation processing apparatus 200, for example, it is possible to apply an apparatus which measures reflectance at specific wavelengths of human skin, and evaluates the measurement result.

For example, in the example shown in FIG. 8, the measuring apparatus 1 according to an embodiment of the present disclosure receives reflected light of the human skin with the light receiving element 101, by irradiating light having N types of wavelengths to the human skin. As a result of this, the light receiving element 101 generates measurement information related to the received reflected light. The measuring apparatus 1 outputs the measurement information generated by the light receiving element 101 to the calculation processing apparatus 200.

A measurement information acquisition section 201 of the calculation processing apparatus 200 acquires the measurement information generated by the measuring apparatus 1 (for example, information such as an arbitrary skin reflection spectrum or reflectance of specific wavelengths) from the measuring apparatus 1, and outputs the acquired information to a calculation section 203.

The calculation section 203 performs calculations in line with Lambert-Beer's law or the like, for example, based on the measurement information acquired by the measurement information acquisition section 201, and calculates the existing amount or the like of various types of substances, which are present within the human skin.

The human skin is a layered structure of the epidermis, dermis and subcutaneous tissues, from a location near to the body surface. Further, by irradiating light on the human skin, and using reflected light which is reflected by the dermis, the existing amount and density can be measured such as for collagen present within the dermis, keratin present within the roots of hairs, and hemoglobin present within the capillaries.

Lambert-Beer's law states that the density of a substance is proportional to the absorbance obtained from a result of measurement, and the absorbance is defined as a common logarithm of the reciprocal of measured permeability. Further, since it is possible for the absorbance to be represented as the product of a particular absorbance coefficient in the substance and the substance amount, it is possible for the substance amount to be ultimately calculated by the following Equation 101.

Physical Amount=Log(1/permeability)/absorbance coefficient  (Equation 101)

Therefore, by using a known so-called density calculation method, based on the measurement result by the measuring apparatus 1 and the above described Equation 101, the calculation section 203 can calculate the existing amount and density of substances to be focused on.

By displaying the measurement result calculated by the calculation section 203 on a display or the like, it becomes possible for the calculation processing apparatus 200 to provide a user with daily changes of the measurement results or the like, based on the included substances to be focused on.

FIG. 9 is an explanatory diagram which schematically shows hemoglobin metabolism within the human body.

Hemoglobin is the generic name of proteins constituted from 4 subunits, which exists within blood. As shown in FIG. 9, these hemoglobins become oxyhemoglobins by connecting with oxygen absorbed from the lungs, for example, and become deoxyhemoglobins by reacting with carbon dioxide by discharging oxygen at various locations within the body. Further, when monosaccharides such as glucose are discharged from the liver or the like to within the blood, hemoglobins become glycohemoglobins by connecting with these monosaccharides. Glycohemoglobins also become deoxyhemoglobins by discharging the connected monosaccharides at various locations within the body. The discharged oxygen and monosaccharides become consumed as energy at various locations within the body. Further, deoxyhemoglobins are dissolved in compounds ($C_{33}H_{36}N_4O_6$) called bilirubin when their lifespan has been reached, are metabolized by the liver, and are excreted to outside of the body.

Here, since the wavelength regions of light absorbed by these substances are slightly different, the oxyhemoglobin, glycohemoglobin and deoxyhemoglobin present within metabolic pathways can measure the density within blood, by focusing on specific wavelengths within the reflected light. The 5 wavelength types of 500 nm, 540 nm, 580 nm, 620 nm and 660 nm shown by an embodiment of the present disclosure function as useful wavelength regions, when the substance amount of these hemoglobins are measured. Therefore, by measuring the reflectance in the above described 5 types of wavelengths by using the measuring apparatus 1 according to an embodiment of the present disclosure, the existing amount and density of oxyhemoglobin, glycohemoglobin, and deoxyhemoglobin can be measured. By providing a user with the existing amount of these included substances, it becomes possible for the user to perform suitably targeted healthcare and observations of physical condition abnormalities.

Hereinafter, an example will be specifically described, in the case where the calculation section 203 calculates the densities of the 4 types of measurement object elements of melanin, deoxyhemoglobin, oxyhemoglobin, and glycohemoglobin, by using measurement data acquired by the measurement information acquisition section 201.

By Lambert-Beer's law, when the measured reflectance is set as t, the density per unit optical path is set as c1 (units: mol/L*cm), and the molar absorbance coefficient is set as $\epsilon$, the following Equation 102 is satisfied.

$$\log(1/t) = \epsilon * c1 \quad \text{(Equation 102)}$$

Further, the molar absorbance coefficient and the density per unit optical path of melanin, deoxyhemoglobin, oxyhemoglobin and glycohemoglobin are represented such as follows.

Melanin

Molar absorbance coefficient: $\epsilon 1$, Density per unit optical path: Mn

Deoxyhemoglobin

Molar absorbance coefficient: $\epsilon 2$, Density per unit optical path: Hb

Oxyhemoglobin

Molar absorbance coefficient: $\epsilon 3$, Density per unit optical path: HbO2

Glycohemoglobin

Molar absorbance coefficient: $\epsilon 4$, Density per unit optical path: HbA1c When the reflectance by wavelengths in the measurement data is represented as S, and an interface reflectance within the human body is represented as D, the following Equation 103 is satisfied per each wavelength to be focused on, by the above described Equation 102.

$$Mn*\epsilon 1 + Hb*\epsilon 2 + HbO2*\epsilon 3 + HbA1c*\epsilon 4 + D = -\log S \quad \text{(Equation 103)}$$

Therefore, by referring to the molar absorbance coefficient of predetermined measurement object elements stored in a storage section 205 or the like, and taking into consideration the above described Equation 103 for each wavelength to be focused on (for example, the 5 wavelengths shown in FIG. 4), the calculation section 203 can obtain a series of simultaneous equations. By solving these simultaneous equations, the calculation section 203 can calculate the densities of the measurement object elements (that is, a density per unit optical path).

The preferred embodiments of the present invention have been described above with reference to the accompanying drawings, whilst the present invention is not limited to the above examples, of course. A person skilled in the art may find various alterations and modifications within the scope of the appended claims, and it should be understood that they will naturally come under the technical scope of the present invention.

Additionally, the present technology may also be configured as below.

(1)

A measuring apparatus, including:

a light receiving element, provided at a position facing a measurement object region on which is placed a measurement object, which forms an image with light from the measurement object region;

a plurality of light emitting elements, arranged surrounding the light receiving element, which emit light for measuring the measurement object; and reflective optical elements, provided above the light emitting elements, which guide, to the measurement object region, emission light radiated from the light emitting elements, wherein a light receiving surface of the light receiving element and light emission surfaces of the plurality of light emitting elements are positioned mutually on a same plane, and wherein the emission light radiated from the plurality of light emitting elements is reflected by the reflective optical elements, and center lines of the emission light radiated from each of the light emitting elements pass through an approximate center of the measurement object region.

(2)

The measuring apparatus according to (1), wherein an opening section is provided in the measurement object region on which is placed the measurement object, and wherein a center of the opening section and a center of the light receiving element face each other.

(3)

The measuring apparatus according to (1) or (2), wherein N light emitting elements are arranged as the plurality of light emitting elements, and wherein radiated emission light of M (M≤N) types of wavelengths are output from the N light emitting elements.

(4)

The measuring apparatus according to any one of (1) to (3), wherein the measurement object is organic matter.

(5)

The measuring apparatus according to (4), wherein the organic matter is skin of a human body.

(6)

The measuring apparatus according to any one of (3) to (5), wherein, in a case where the number of the plurality of light emitting elements is greater than the number of types of wavelengths of the radiated emission light emitted from the light emitting elements, wavelengths of the radiated emission light are selected in an order from a wavelength with a narrowest allowable wavelength width.

(7)

The measuring apparatus according to any one of (1) to (6), wherein a light amount of light reflected from the measurement object and received by the light receiving element is 95% or more on the basis of a light amount of light reflected from a white calibration plate in the case where the white calibration plate is placed as the measurement object.

(8)

The measuring apparatus according to (7), wherein a separation distance between the light receiving element and the measurement object is 3±0.2 mm, wherein a size of the light receiving element is 10 mm on all sides, and wherein a size of the opening section having a circular shape is a diameter of 5±0.4 mm.

(9)

The measuring apparatus according to (8), wherein a numerical aperture NA of the radiated emission light is 0.2, and wherein an installation angle is 51° for the light emission surfaces of the reflective optical elements.

(10)

The measuring apparatus according to (9), wherein a number of the light emitting elements is 8, wherein wavelengths of the radiated emission light emitted from the light emitting elements are five types of $\lambda_1$: 500±25 nm, $\lambda_2$: 540±15 nm, $\lambda_3$: 580 nm±5 nm, $\lambda_4$: 620±15 nm, and $\lambda_5$: 660±15 nm, wherein one of each of the light emitting elements for respectively emitting the wavelengths of $\lambda_1$ and $\lambda_2$ are provided, and wherein two of each of the light emitting elements for respectively emitting the wavelengths of $\lambda_3$ to $\lambda_5$ are provided.

(11)

A measuring method, including:

emitting light for measuring a measurement object, from a plurality of light emitting elements which emit light for measuring the measurement object, arranged surrounding a light receiving element provided at a position facing a measurement object region on which is placed the measurement object, the light receiving element forming an image with light from the measurement object region;

guiding, to the measurement object region, radiated emission light emitted from each of the plurality of light emitting elements by reflective optical elements provided above the light emitting elements, so that center lines of the radiated emission light pass through an approximate center of the measurement object region; and receiving light reflected from the measurement object region by the light receiving element, wherein a light receiving surface of the light receiving element and light emission surfaces of the plurality of light emitting elements are positioned mutually on a same plane.

(12)

A parameter setting method, including:

setting, in a measuring apparatus, a minimum value of a light amount of light reflected from a measurement object and received by a light receiving element, and determining a size of the light receiving element on the basis of the set minimum value of the light amount of reflected light, the measuring apparatus including the light receiving element provided at a position facing a measurement object region on which is placed the measurement object, the light receiving element forming an image with light from the measurement object region, a plurality of light emitting elements that are arranged surrounding the light receiving element and that emit light for measuring the measurement object, and reflective optical elements that are provided above the light emitting elements and that guide, to the measurement object region, emission light radiated from the light emitting elements, wherein a light receiving surface of the light receiving element and light emission surfaces of the plurality of light emitting elements are positioned mutually on a same plane, and wherein the light radiated from the plurality of light emitting elements is reflected by the reflective optical elements, and center lines of the emission light radiated from each of the light emitting elements pass through an approximate center of the measurement object region; and setting a size of the measurement object region based on a signal-to-noise ratio necessary for the light receiving element and the set minimum value of the light amount of reflected light, and setting a separation distance between the light receiving element and the measurement object based on a light amount incident on the light receiving element and the minimum value of the light amount of reflected light.

REFERENCE SIGNS LIST

1 Measuring apparatus
11 Housing

13 Opening section
100 Optical system
101 Light receiving element
103 Light emitting elements
105 Reflective optical elements (mirrors)
200 Calculation processing apparatus
201 Measurement information acquisition section
203 Calculation section
205 Storage section

The invention claimed is:

1. A measuring apparatus, comprising:
a light receiving element, provided at a position facing a measurement object region on which is placed a measurement object, which forms an image with light from the measurement object region;
a plurality of light emitting elements, arranged surrounding the light receiving element, which emit light for measuring the measurement object; and
reflective optical elements, provided above the light emitting elements, which guide, to the measurement object region, emission light radiated from the light emitting elements,
wherein a light receiving surface of the light receiving element and light emission surfaces of the plurality of light emitting elements are positioned mutually on a same plane, and
wherein the emission light radiated from the plurality of light emitting elements is reflected by the reflective optical elements, and center lines of the emission light radiated from each of the light emitting elements pass through an approximate center of the measurement object region.

2. The measuring apparatus according to claim 1,
wherein an opening section is provided in the measurement object region on which is placed the measurement object, and
wherein a center of the opening section and a center of the light receiving element face each other.

3. The measuring apparatus according to claim 2,
wherein N light emitting elements are arranged as the plurality of light emitting elements, and
wherein the radiated emission light of M (M≤N) types of wavelengths are output from the N light emitting elements.

4. The measuring apparatus according to claim 1,
wherein the measurement object is organic matter.

5. The measuring apparatus according to claim 4,
wherein the organic matter is skin of a human body.

6. The measuring apparatus according to claim 3,
wherein, in a case where the number of the plurality of light emitting elements is greater than the number of types of wavelengths of the radiated emission light emitted from the light emitting elements, wavelengths of the radiated emission light are selected in an order from a wavelength with a narrowest allowable wavelength width.

7. The measuring apparatus according to claim 1,
wherein a light amount of light reflected from the measurement object and received by the light receiving element is 95% or more on the basis of a light amount of light reflected from a white calibration plate in the case where the white calibration plate is placed as the measurement object.

8. The measuring apparatus according to claim 7,
wherein a separation distance between the light receiving element and the measurement object is 3±0.2 mm,
wherein a size of the light receiving element is 10 mm on all sides, and
wherein a size of a circular opening section is a diameter of 5±0.4 mm.

9. The measuring apparatus according to claim 8,
wherein a numerical aperture NA of the radiated emission light is 0.2, and
wherein an installation angle is 51° for the light emission surfaces of the reflective optical elements.

10. The measuring apparatus according to claim 9,
wherein a number of the light emitting elements is 8,
wherein wavelengths of the radiated emission light emitted from the light emitting elements are five types of $\lambda_1$: 500±25 nm, $\lambda_2$: 540±15 nm, $\lambda_3$: 580 nm±5 nm, $\lambda_4$: 620±15 nm, and $\lambda_5$: 660±15 nm,
wherein one of each of the light emitting elements for respectively emitting the wavelengths of $\lambda_1$ and $\lambda_2$ are provided, and
wherein two of each of the light emitting elements for respectively emitting the wavelengths of $\lambda_3$ to $\lambda_5$ are provided.

11. A measuring method, comprising:
emitting light for measuring a measurement object, from a plurality of light emitting elements which emit light for measuring the measurement object, arranged surrounding a light receiving element provided at a position facing a measurement object region on which is placed the measurement object, the light receiving element forming an image with light from the measurement object region;
guiding, to the measurement object region, radiated emission light emitted from each of the plurality of light emitting elements by reflective optical elements provided above the light emitting elements, so that center lines of the radiated emission light pass through an approximate center of the measurement object region; and
receiving light reflected from the measurement object region by the light receiving element,
wherein a light receiving surface of the light receiving element and light emission surfaces of the plurality of light emitting elements are positioned mutually on a same plane.

12. A parameter setting method, comprising:
setting, in a measuring apparatus, a minimum value of a light amount of light reflected from a measurement object and received by a light receiving element, and determining a size of the light receiving element on the basis of the set minimum value of the light amount of reflected light, the measuring apparatus including the light receiving element provided at a position facing a measurement object region on which is placed the measurement object, the light receiving element forming an image with light from the measurement object region, a plurality of light emitting elements that are arranged surrounding the light receiving element and that emit light for measuring the measurement object, and reflective optical elements that are provided above the light emitting elements and that guide, to the measurement object region, emission light radiated from the light emitting elements, wherein a light receiving surface of the light receiving element and light emission surfaces of the plurality of light emitting elements are positioned mutually on a same plane, and wherein the light radiated from the plurality of light emitting elements is reflected by the reflective optical elements, and center lines of the emission light radiated from each of the light emitting elements pass through an approximate center of the measurement object region; and setting a size of the measurement object region based on a signal-to-noise ratio necessary for the light receiving element and the set minimum value of the light amount of reflected light, and setting a separation distance between the light receiving element and the measurement object based on a light amount incident on the light receiving element and the minimum value of the light amount of reflected light.

\* \* \* \* \*